(12) United States Patent
Tanabe et al.

(10) Patent No.: US 6,358,502 B1
(45) Date of Patent: *Mar. 19, 2002

(54) HAIR COSMETIC COMPOSITIONS CONTAINING GLYCINE AND ALANINE

(75) Inventors: Hisateru Tanabe; Shinobu Nagase; Satoshi Shibuichi; Kenji Arai, all of Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/465,449

(22) Filed: Dec. 17, 1999

(30) Foreign Application Priority Data

Dec. 28, 1998 (JP) .............................. 10-374708
Jan. 26, 1999 (JP) ............................. 11-017492

(51) Int. Cl.⁷ .......................... A61K 7/06; A61K 7/075; A61K 7/08
(52) U.S. Cl. ............... 424/70.28; 424/70.1; 424/70.11; 424/70.12; 424/70.27; 510/119; 510/127
(58) Field of Search .............................. 424/70.1, 70.11, 424/70.12, 70.13, 70.27, 70.28; 510/119, 127

(56) References Cited

U.S. PATENT DOCUMENTS 4,855,130 A 8/1989 Konrad et al.
5,712,232 A 1/1998 Moriyama et al.
6,228,353 B1 * 5/2001 Carr et al.

FOREIGN PATENT DOCUMENTS

| DE | 195 04 914 | | 11/1995 |
| DE | 195 33 211 | | 2/1996 |
| EP | 0 793 956 | | 9/1997 |
| EP | 0 858 794 | | 9/1998 |
| GB | 1 401 089 | * | 7/1975 |
| GB | 2 322 550 | * | 9/1998 |

OTHER PUBLICATIONS

Patent Abstracts of Japan, vol. 1998, No. 08, Feb. 27, 1998, JP 09 301831, Nov. 25, 1997.

Patent Abstracts of Japan, vol. 1997. No. 08, Aug. 29, 1997, JP 09 100218, Apr. 15, 1997.

* cited by examiner

*Primary Examiner*—Gollamudl S. Kishore
*Assistant Examiner*—Brian K. Seidleck
(74) *Attorney, Agent, or Firm*—Oblon, Spivak, McClelland, Maier & Neustadt, P.C.

(57) ABSTRACT

This invention relates a hair cosmetic composition, which comprises (A) glycine or alanine, (B) an α-hydroxy acid, β-hydroxy acid, 1,2-dicarboxylic acid, 1,3-dicarboxylic acid or aromatic carboxylic acid, and (C) a cationic surfactant. The hair cosmetic composition is excellent in the effect of improving optical or mechanical properties of hair.

14 Claims, No Drawings

HAIR COSMETIC COMPOSITIONS CONTAINING GLYCINE AND ALANINE

TECHNICAL FIELD

This invention relates to a hair cosmetic composition excellent in the effect of improving optical or mechanical properties of hair.

BACKGROUND ART

A variety of hair cosmetic compositions containing cationic surfactants have been used for many years to improve optical or mechanical properties of hair, such as luster, softness, body and the like. Effects of these hair cosmetic compositions are however either temporary or insufficient.

JP 10-236927 A discloses a hair treatment composition for supplying a precursor of a hair-united lipofatty acid to hair follicles, in which (i) a first fatty acid precursor selected from leucine, isoleucine, methionine or valine, (ii) a second fatty acid precursor selected from a saccharide or a mono-, di- or tri-carboxylic acid and (iii) an anionic, amphoteric or cationic surfactant has been added. However, this invention was created by drawing a hint from the fact that the above-described components (i) and (ii) act as a precursor of a hair-united lipofatty acid for hair follicles. It is therefore impossible to predict from this invention what components should be added for the improvement of optical or mechanical properties of hair.

The present invention therefore has as an object the provision of a hair cosmetic composition excellent in the effect of improving optical or mechanical properties of hair.

DISCLOSURE OF THE INVENTION

The present inventors have found that combined use of glycine or alanine and a specific acid compound with an cationic surfactant makes it possible to obtain a hair cosmetic composition excellent in the effect of improving optical or mechanical properties of hair such luster, softness, body and the like.

This invention therefore provides a hair cosmetic composition comprising (A) glycine or alanine, (B) an α-hydroxy acid, β-hydroxy acid, 1,2-dicarboxylic acid, 1,3-dicarboxylic acid or aromatic carboxylic acid, and (C) a cationic surfactant.

BEST MODE FOR CARRYING OUT THE INVENTION

The component (A) for use in the present invention is glycine or alanine. Of these, particularly preferred are glycine and α-alanine.

As the component (A), glycine and alanine may be used in combination. The component (A) may be added preferably in a proportion of from 0.01 to 20 wt. %, more preferably from 0.05 to 10 wt. %, notably from 0.1 to 5 wt. % based on the whole composition from the standpoint of imparting color deepness to hair.

Among acids usable as the component (B) in the present invention, illustrative α-hydroxy acids and β-hydroxy acids can include glycolic acid, lactic acid, methylacetic acid, mandelic acid, 4-hydroxymandelic acid, 3-hydroxy-4-methoxymandelic acid, 4-hydroxy-3-methoxymandelic acid, 3-(2-hydroxyphenyl)lactic acid, 3-(4'-hydroxyphenyl) lactic acid, 3,4-dihydromandelic acid, glyceric acid, malic acid, tartaric acid, and citric acid.

Further, illustrative 1,2-dicarboxylic acids and 1,3-dicarboxylic acids can include malonic acid, succinic acid, maleic acid, and fumaric acid. Illustrative aromatic carboxylic acids can include benzoic acid, phthalic acid, and salicylic acid.

Among these, malic acid, succinic acid and maleic acid are particularly preferred.

As the component (B), one or more of the above-described acids can be used. The component (B) may be added preferably in a proportion of from 0.01 to 5 wt. %, more preferably from 0.05 to 3 wt. %, notably from 0.1 to 2 wt. % based on the whole composition from the standpoint of imparting transparency to hair.

The cationic surfactant for use as the component (C) in the present invention can be, for example, a quaternary ammonium salt represented by the following formula (1):

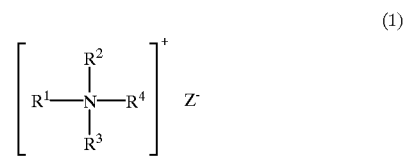

wherein at least one of $R^1$, $R^2$, $R^3$ and $R^4$ represents an alkyl or alkenyl group, which may optionally be substituted by one or more alkoxy, alkenyloxy, alkanoylamino or alkenoylamino groups and has 8 to 28 carbon atoms in total, the remaining one or ones each independently represent a benzyl group, an alkyl or hydroxyalkyl group having 1 to 5 carbon atoms or a polyoxyethylene group having a total added mole number not greater than 10, and $Z^-$ represents a halogen ion or an organic anion.

Among such quaternary ammonium salts, preferred are those represented by the formula (1) in which one or two of $R^1$, $R^2$, $R^3$ and $R^4$ each independently represent a linear or branched alkyl group having 12 to 24 carbon atoms or a benzyl group, the remaining ones each independently represent a methyl group, and $Z^-$ represents a halogen ion; and particularly preferred as those represented by the formula (1) in which one of $R^1$, $R^2$, $R^3$ and $R^4$ represents a linear or branched alkyl group having 12 to 22 carbon atoms, the remaining ones each independently represent a methyl group, and $Z^-$ represents a halogen ion.

These cationic surfactants may be used either singly or in combination. The cationic surfactant may be added preferably in a proportion of from 0.1 to 20 wt. %, more preferably from 0.2 to 10 wt. %, notably from 0.5 to 5 wt. % based on the whole composition from the standpoint of imparting softness to hair.

To the hair cosmetic composition according to the present invention, (D) a higher alcohol can be added further. This higher alcohol can improve the touch of hair further.

Examples of the higher alcohols are those having 6 to 30 carbon atoms, with 8 to 22 carbon atoms being preferred. Further, those having melting points not higher than 55° C. are preferred.

Such higher alcohols may be used either singly or in combination. The higher alcohol is added in a proportion of from 3 to 10 molar times, preferably from 4 to 8 molar times of the cationic surfactant added as the component (C).

To the hair cosmetic composition according to the present invention, (E) a silicone can be added further. This silicone can provide hair with nongreasiness.

Preferred examples of the silicone are methylpolysiloxanes represented by the following formula (2):

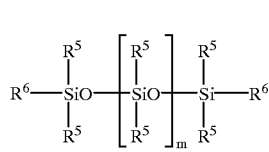

wherein $R^5$ represents a methyl or phenyl group, $R^6$ represents a methyl or hydroxyl group, and m stands for a number of from 100 to 2,000.

These silicones may be used either singly or in combination. The silicone may be added preferably in a proportion of from 0.01 to 10 wt. %, more preferably from 0.05 to 10 wt. %, notably 0.1 to 5 wt. % based on the whole composition.

To the hair cosmetic composition according to the present invention, surfactants other than those described above, cationic polymers, cosmetic oils, dyes, reducing agents, oxidizing agents, metal chelates, antioxidants, viscosity modifiers, preservatives, animal and plant extracts, antiphlogistics, disinfectants, antidandruff agents, oxidation inhibitors, pearlants, ultraviolet absorbers, pH regulators, colors, solvent, perfumes and the like can be added as desired in addition to the above-described components.

The pH of the hair cosmetic composition according to the present invention may preferably be not higher than the pKa of the α-hydroxy acid (B) employed, and may range specifically from 2 to 6, with pH 2.5 to 3.5 being particularly preferred.

The hair cosmetic composition according to the present invention can be produced by an ordinary method and can be used, for example, as a hair rinse, conditioner, treatment, hair cream, hair pack or the like

EXAMPLE 1

Conditioners were prepared by mixing their corresponding components shown in Table 1, and the external appearance, softness/body, manageability and touch of hair when the shampoos were used were ranked. In each ranking, permed and bleached hair samples were used. The results are also presented in Table 1.

(Ranking Method)

After bundles of hair, each of which was 20 cm in length and 10 g in weight, were washed with a commercial shampoo ("Lavenus Cleansing Shampoo", trade mark; product of Kao Corp.), 3-gram portions of the individual conditioners were applied to the bundles of hair, respectively. After the bundles of hair were left over for 30 minutes, they were rinsed with warm water of 40° C. Subsequent to drying, they were organoleptically ranked in comparison with untreated bundles of hair by ten expert panellers in accordance with the following ranking standards.

| <External appearance of hair> | |
|---|---|
| Deep in luster and color, high transparency, and shiny | +1 point |
| Cannot be said good or bad | 0 point |
| Lackluster, timid color, no transparency, and dry and loose | −1 point |

Based on the total points of all the panellers, each sample acquired +4 points or more was ranked "A", each sample acquired +3 to −3 points was ranked "B", and each sample acquired −4 point or less was ranked "C".

| <Softening/body> | |
|---|---|
| Soft and silky touch with adequate resiliency, and good body | +1 point |
| Cannot be said good or bad | 0 point |
| Poor body and no silky touch | −1 point |

Based on the total points of all the panellers, each sample acquired +4 points or more was ranked "A", each sample acquired +3 to −3 points was ranked "B", and each sample acquired −4 point or less was ranked "C".

| <Manageability of hair> | |
|---|---|
| Well managed without hair out of place | +1 point |
| Cannot be said good or bad | 0 point |
| Not managed with hair out of place | −1 point |

Based on the total points of all the panellers, each sample acquired +4 points or more was ranked "A", each sample acquired +3 to −3 points was ranked "B", and each sample acquired −4 point or less was ranked "C".

| <Touch> | |
|---|---|
| Silky touch | +1 point |
| Cannot be said good or bad | 0 point |
| No silky touch | −1 point |

Based on the total points of all the panellers, each sample acquired +4 points or more was ranked "A", each sample acquired +3 to −3 points was ranked "B", and each sample acquired −4 point or less was ranked "C".

TABLE 1

| Component (wt. %) | Invention product | | | | | | | Comparative product | | |
|---|---|---|---|---|---|---|---|---|---|---|
| | 1 | 2 | 3 | 4 | 5 | 6 | 7 | 1 | 2 | 3 |
| Stearyltrimethylammonium chloride | 1.0 | | | | | | | 1.0 | | |
| Diacetyldimethylammonium chloride | | 1.0 | | | 0.5 | | | | 1.0 | |
| Behenyltrimethylammonium chloride | | | 1.0 | 1.0 | 0.5 | 1.0 | 1.0 | | | 1.0 |

TABLE 1-continued

|  | Invention product | | | | | | | Comparative product | | |
|---|---|---|---|---|---|---|---|---|---|---|
| Component (wt. %) | 1 | 2 | 3 | 4 | 5 | 6 | 7 | 1 | 2 | 3 |
| Cetearyl alcohol | 3.0 | 3.0 | 3.0 |  | 3.0 | 3.0 | 3.0 | 3.0 | 3.0 | 3.0 |
| Glycine | 1.0 | 1.0 | 1.0 | 1.0 | 1.0 | 2.0 |  |  |  |  |
| α-Alanine |  |  |  |  |  |  | 1.0 |  |  |  |
| Malic acid | 0.5 | 0.5 | 0.5 | 0.5 |  |  | 0.5 |  |  |  |
| Maleic acid |  |  |  |  | 0.5 |  |  |  |  |  |
| Succinic acid |  |  |  |  |  | 0.5 |  |  |  | 0.5 |
| pH regulator (HCl) |  |  |  |  |  |  |  | q.s. | q.s. | q.s |
| Perfume | 0.5 | 0.5 | 0.5 | 0.5 | 0.5 | 0.5 | 0.5 | 0.5 | 0.5 | 0.5 |
| Water | Balance | Balance | Balance | Balance | Balance | Balance | Balance | Balance | Balance | Balance |
| pH | 3.3 | 3.3 | 3.3 | 3.3 | 3.3 | 3.3 | 3.3 | 5.5 | 5.5 | 5.0 |
| Hair external appearance | A | A | A | A | A | A | A | C | C | B |
| Softening/body | C | C | C | C | C | C | A | B | A | B |
| Hair manageability | A | A | A | A | A | A | A | C | C | B |
| Touch | A | A | A | B | A | A | A | C | B | B |

EXAMPLE 2

Conditioners (Invention Products 8–14; pH 3.3) were prepared in a similar manner as Invention Products 1–7 in Example 1 except that methylpolysiloxane ("KF96A 5,000 cs", trade name; product of Shin-Etsu Chemical Co., Ltd.) was additionally incorporated in a proportion of 1 wt. %.

With respect to the conditioners so obtained, their external appearance of hair, softening/body, hair manageability and touch were ranked. Invention Products 8–14 all gave similar results as in Example 1. In addition, they were also organoleptically ranked for the nongreasiness of hair in a similar manner as in Example 1 in accordance with the following ranking standard.

| <Nongreasiness of hair> | |
|---|---|
| Nongreasy | +1 point |
| Cannot be said good or bad | 0 point |
| Lack of nongreasiness | −1 point |

Based on the total points of all the panellers, each sample acquired +4 points or more was ranked "A", each sample acquired +3 to −3 points was ranked "B", and each sample acquired −4 point or less was ranked "C".

As a result, Invention Products 8–14 were all ranked "A" in the nongreasiness of hair.

EXAMPLE 3

(Treatment)

A treatment (pH 3.5) of the following formulation was prepared by a method known per se in the art.

| (Components) | (wt. %) |
|---|---|
| Behenyltrimethylammonium chloride | 2.0 |
| Cetaryl alcohol | 5.0 |
| Glycine | 1.0 |
| Malic acid | 0.5 |
| Methylparaben | 0.1 |
| Perfume | 0.5 |
| Water | Balance |

EXAMPLE 4

(Conditioning Foam)

A conditioning foam (pH 3.5) of the following formulation was prepared by a method known per se in the art.

| (Components) | (wt. %) |
|---|---|
| Behenyltrimethylammonium chloride | 0.3 |
| Cetaryl alcohol | 1.0 |
| Glycine | 1.0 |
| Malic acid | 0.5 |
| Methylparaben | 0.1 |
| Perfume | 0.5 |
| LPG | 10.0 |
| Water | Balance |

EXAMPLE 5

(Hair Cream)

A hair cream (pH 3.0) of the following formulation was prepared by a method known per se in the art.

| (Components) | (wt. %) |
|---|---|
| Behenyltrimethylammonium chloride | 1.5 |
| PEG-20 sorbitan monostearate | 0.5 |
| Cetaryl alcohol | 3.0 |
| Liquid paraffin | 5.0 |
| PEG-3 2-ethylhexanoate | 2.5 |
| Glycine | 1.0 |
| Malic acid | 0.5 |
| Perfume | 0.5 |
| Hydroxypropylcellulose (1% solution, viscosity: 6 Pa · s) | 0.3 |
| Water | Balance |

The hair cosmetic compositions obtained in Examples 3–5 all imparted good luster, softness and body to hair, and also improved the manageability of hair.

Capability of Exploitation in Industry

Hair cosmetic compositions according to the present invention have excellent cleansing power and can significantly improve optical or mechanical properties of hair. They impart color deepness, transparency and shiny luster. They also impart softness and body to hair, so that the manageability of hair is improved.

What is claimed is:

1. A hair cosmetic composition comprising:
   (A) alanine;
   (B) an acid selected from the group consisting of malic acid, maleic acid and a mixture thereof; and
   (C) a cationic surfactant.

2. A hair cosmetic composition according to claim 1, wherein said cationic surfactant (C) is a quaternary ammonium salt represented by the following formula (1):

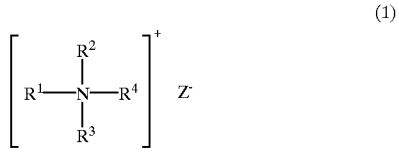

(1)

wherein at least one of $R^1$, $R^2$, $R^3$ and $R^4$ represents an alkyl or alkenyl group, which may optionally be substituted by one or more alkoxy, alkenyloxy, alkanoylamino or alkenoylamino groups and has 8 to 28 carbon atoms in total, the remaining one or ones each independently represent a benzyl group, an alkyl or hydroxyalkyl group having 1 to 5 carbon atoms or a polyoxyethylene group having a total added mole number not greater than 10, and $Z^-$ represents a halogen ion or an organic anion.

3. A hair cosmetic composition according to claim 1 or 2, further comprising (D) a higher alcohol in a proportion of from 3 to 10 molar times of said component (C).

4. A hair cosmetic composition according to claim 1 or 2, further comprising (E) a silicone.

5. The hair cosmetic composition of claim 1, wherein alanine is containing in an amount of from 0.01 to 20 wt. %.

6. The hair cosmetic composition of claim 5, wherein component (B) is containing in an amount of from 0.01 to 5 wt. %.

7. The hair cosmetic composition of claim 5, wherein component (C) is containing in an amount of from 0.1 to 20 wt. %.

8. A hair cosmetic composition comprising:
   (A) glycine
   (B) an acid selected from the group consisting of malic acid, maleic acid and a mixture thereof; and
   (C) a cationic surfactant.

9. The hair cosmetic composition according to claim 8, wherein said cationic surfactant (C) is a quaternary ammonium salt represented by the following formula (1):

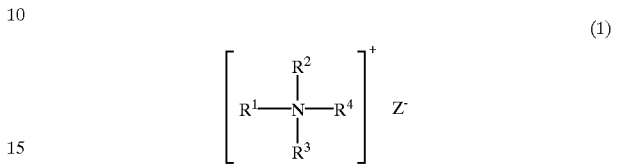

(1)

wherein at least one of $R^1$, $R^2$, $R^3$ and $R^4$ represents an alkyl or alkenyl group, which may optionally be substituted by one or more alkoxy, alkenyloxy, aklanoylamino or alkenoylamino groups and has 8 to 28 carbon atoms in total, the remaining one or ones each independently represent a benzyl group, an alkyl or hydroxyalkyl group having 1 to 5 carbon atoms or a polyoxyethylene group having a total added mole number not greater than 10, and $Z^-$ represents a halogen ion or an organic anion.

10. The hair cosmetic composition of claim 8, further comprising (D) a higher alcohol in a proportion of from 3 to 10 molar time s of said component (C).

11. The hair cosmetic composition of claim 8, further comprising (E) a silicone.

12. The hair cosmetic composition of claim 8, wherein glycine is containing in an amount of from 0.01 to 20 wt. %.

13. The hair cosmetic composition of claim 8, wherein component (B) is containing in an amount of from 0.01 to 5 wt. %.

14. The hair cosmetic composition of claim 8, wherein component (C) is containing in an amount of from 0.1 to 20 wt. %.

\* \* \* \* \*

UNITED STATES PATENT AND TRADEMARK OFFICE
CERTIFICATE OF CORRECTION

PATENT NO. : 6,358,502 B1
DATED : March 19, 2002
INVENTOR(S) : Hisateru Tanabe et al.

It is certified that error appears in the above-identified patent and that said Letters Patent is hereby corrected as shown below:

<u>Column 8,</u>
Line 20, "aklanoyolamino", should read -- alkanoylamino --.
Line 29, "time s", should read -- times --.

Signed and Sealed this

Thirtieth Day of July, 2002

Attest:

JAMES E. ROGAN
Attesting Officer
Director of the United States Patent and Trademark Office